(12) United States Patent
Lemieux et al.

(10) Patent No.: US 10,621,384 B2
(45) Date of Patent: Apr. 14, 2020

(54) METHOD AND SYSTEM OF CONSTRAINT-BASED OPTIMIZATION OF DIGITAL HUMAN UPPER LIMB MODELS

(71) Applicant: Dassault Systemes Americas Corp., Waltham, MA (US)

(72) Inventors: Pierre-Olivier Lemieux, Montreal (CA); Arnaud Barré, Montreal (CA); Rachid Aissaoui, Montreal (CA); Nicola Hagemeister, Montreal (CA)

(73) Assignee: Dassault Systemes Americas Corp., Waltham, MA (US)

( * ) Notice: Subject to any disclaimer, the term of this patent is extended or adjusted under 35 U.S.C. 154(b) by 316 days.

(21) Appl. No.: 14/963,679

(22) Filed: Dec. 9, 2015

(65) Prior Publication Data

US 2017/0169138 A1 Jun. 15, 2017

(51) Int. Cl.
 *G06F 17/50* (2006.01)
 *G06F 30/20* (2020.01)
 *G16H 50/50* (2018.01)

(52) U.S. Cl.
 CPC .............. *G06F 30/20* (2020.01); *G16H 50/50* (2018.01)

(58) Field of Classification Search
 CPC .................................................. G06F 17/5009
 See application file for complete search history.

(56) References Cited

U.S. PATENT DOCUMENTS

| | | | |
|---|---|---|---|
| 2003/0100366 A1 | 5/2003 | Nagase | |
| 2004/0263518 A1* | 12/2004 | Anderson | G06T 13/40 345/473 |
| 2006/0061574 A1* | 3/2006 | Ng-Thow-Hing | G06T 13/40 345/473 |
| 2010/0030532 A1* | 2/2010 | Arora | G06F 17/5009 703/2 |
| 2011/0298800 A1 | 12/2011 | Schlichte | |
| 2013/0079928 A1* | 3/2013 | Soe-Knudsen | B25J 9/1656 700/248 |

(Continued)

OTHER PUBLICATIONS

Charbonnier et al, A patient-specific measurement technique to model shoulder joint kinematics, Orthopaedics and Traumatology: Surgery and Research 100 (2014) 715-719.*

(Continued)

*Primary Examiner* — Rehana Perveen
*Assistant Examiner* — Chuen-Meei Gan
(74) *Attorney, Agent, or Firm* — Hamilton, Brook, Smith & Reynolds, P.C.

(57) ABSTRACT

An upper limb model of a virtual manikin includes a data conversion engine configured to produce converted data based on one or more data sets. Each data set represents dependencies between elements of the kinematic model. The upper limb model further includes a kinematic chain model configured to generate one or more constraints based on the converted data. The upper limb model also includes a posturing engine configured to determine, based on the one or more constraints, a trajectory from a first position to a second position. The kinematic model may further include a rendering engine configured to render a posture corresponding to the second posture. The elements of the kinematic model may include one or more of a clavicle, a scapula, a humerus, a forearm and a hand.

16 Claims, 12 Drawing Sheets

(56) References Cited

U.S. PATENT DOCUMENTS

| | | | |
|---|---|---|---|
| 2013/0230838 A1* | 9/2013 | Iannotti | G09B 23/30 |
| | | | 434/262 |
| 2014/0287389 A1* | 9/2014 | Kallmann | G06F 19/3481 |
| | | | 434/247 |
| 2017/0061043 A1 | 3/2017 | Lemieux et al. | |

OTHER PUBLICATIONS

Maurel et al, Human shoulder modeling including scapulo-thoracic constraint and joint sinus cones, Computer and Graphics 24 (2000) 203-218.*
Levasseur et al, The effect of axis alignment on shoulder joint kinematics analysis during arm abduction, Clinical Biomechanics 22 (2007) 758-766.*
Camilo Cortes et al, Upper Limb Posture Estimation in Robotic and Virtual Reality-Based Rehabilitation, Hindawi Publishing Corporation BioMed Research International vol. 2014, Article ID 821908, 18 pages (Year: 2014).*
Lemieux, Pierre-Olivier, et al. "Degrees of freedom coupling adapted to the upper limb of a digital human model." International Journal of Human Factors Modelling and Simulation; 5.4 (2017): 314-337. (Year: 2017).*
N. Hagemeister, M. Senk, R. Dumas & L. Cheze (2011) Effect of axis alignment on in vivo shoulder kinematics, Computer Methods in Biomechanics and Biomedical Engineering, 14:8, 755-761, (Year: 2011).*
P. O. Lemieux, N. Hagemeister, P. Tetreault & N. Nuno (2013) Influence of the medial offset of the proximal humerus on the glenohumeral destabilising forces during arm elevation: a numerical sensitivity study, Computer Methods in Biomechanics and Biomedical Engineering, 16:1, 103-111, (Year: 2013).*
Ludewig et al, Three-Dimensional Clavicular Motion During Arm Elevation: Reliability and Descriptive Data, Journal of Orthopaedic & Sports Physical Therapy 2004 Journal of Orthopaedic & Sports Physical Therapy (Year: 2004).*
Pierre-Olivier Lemieux et al, Mechanical analysis of cuff tear arthropathy during multiplanar elevation with the AnyBody shoulder model, Clinical Biomechanics 27 (2012) 801-806 (Year: 2012).*
Walter Maurel, Daniel Thalmann, Human shoulder modeling including scapulo-thoracic constraint and joint sinus cones Computers & Graphics 24 (2000) (Year: 2000).*
Prinold, Joe Al, and Anthony MJ Bull. "Scaling and kinematics optimisation of the scapula and thorax in upper limb musculoskeletal models." Journal of biomechanics 47, No. 11 (2014): 2813-2819. (Year: 2014).*
Margaret Schenkman, Kinesiology of the Shoulder Complex 1987 Journal of Orthopaedic & Sports Physical Therapy (Year: 1987).*
Zhibin, Song, Ma Tianyu, Nie Chao, and Niu Yijun. "A New Skeleton Model and the Motion Rhythm Analysis for Human Shoulder Complex Oriented to Rehabilitation Robotics." Applied bionics and biomechanics 2018 (2018). (Year: 2018).*
Zhibin, Song, Ma Tianyu, Nie Chao, and Niu Yijun. "A New Skeleton Model and the Motion Rhythm Analysis for Human Shoulder Complex Oriented to Rehabilitation Robotics." Applied bionics and biomechanics 2018 (2018). (Year: 2018).*
Bailey, I.L. and Lovie, J.E., "New Design Principles for Visual Acuity Letter Charts," American Journal of Optometry & Physiological Optics, 53(11): p. 740-745, Nov. 1976.
Duffy, V.G., "Introduction, in Handbook of Digital Human Modeling: Research for Applied Ergonomics and Human Factors Engineering," V.G. Duffy, Editor 2008, CRC Press, Inc.: Boca Raton, Florida, p. 1-8 (table of contents included only), Nov. 2008.
Marler, T., Farrell, K., Kim, J., Rahmatalla, S., Abdel-Malek, K., "Vision Performance Measures for Optimization-Based Posture Prediction," in Digital Human Modeling for Design and Engineering Conference 2006, SAE International: Lyon, France, p. 1-12, Jul. 2006, technical paper No. 2006-01-2334.

de Groot, J.H., and Brand, R., "A three-dimensional regression model of the shoulder rhythm," Clin Biomech (Bristol, Avon), Nov. 2001. 16(9): p. 735-743.
Grewal, T.-J. and Dickerson, C.R., "A novel three-dimensional shoulder rhythm definition that includes overhead and axially rotated humeral postures," Journal of Biomechanics, Feb. 2013, 46(3): p. 608-611.
Inman, V.T., Saunders, J.B., and Abbott, L.C., "Observations on the Function of the Shoulder Joint," Clin Orthop Relat Res, Jan. 1944, 26(1): p. 1-30.
Ludewig, P.M., et al., "Motion of the Shoulder Complex During Multiplanar Humeral Elevation," J Bone Joint Surg Am, Feb. 2009, 91(2): p. 378-389.
McClure, P.W., et al., "Direct 3-dimensional measurement of scapular kinematics during dynamic movements in vivo," J Shoulder Elbow Surg, May/Jun. 2001, 10(3): p. 269-277.
Wang, X., et al., "Three-dimensional modelling of the motion range of axial rotation of the upper arm," J Biomech, Jun. 1998, 31(10): p. 899-908.
Delfs, N., "Manikin in Time; Development of the Virtual Manikin with External Root and Improved Inverse Kinematics," in Mathematical Sciences, May 2012, University of Gothenburg: Gothenburg. p. 40.
Christiensen, J.M. and J.W. McBarron, Man-Systems Integration Standards (NASA-STD-3000), N.A.a.S. Administration, Editor. 1989, National Aeronautics and Space Administration: Houston, TX, USA.
Diffrient, N., A. Tilley, and D. Harman, *Humanscale 7/8/9*. 1981, Massachusetts Institute of Technology: Cambridge, MA. p. 52.
Engin, A.E. and Chen, S.-M., "Statistical Data Base for the Biomechanical Properties of the Human Shoulder Complex—I: Kinematics of the Shoulder Complex," J Biomech Eng, Aug. 1986, 108(3): p. 215-221.
Tumer, S.T. and Engin, A.E., "Three-Dimensional Kinematic Modelling of the Human Shoulder Complex—Part II: Mathematical Modelling and Solution Via Optimization," J Biomech Eng, May 1989. 111(2): p. 113-121.
Gehrmann, S.V., Kaufmann, R.A., and Li, Z.M., "Wrist Circumduction Reduced by Finger Constraints," J Hand Surg Am, Apr. 2008. 33(8): p. 1287-1292.
Edelsbrunner, H., Kirkpatrick, D., and Seidel, R., "On the Shape of a Set of Points in the Plane," Information Theory, IEEE Transactions on, Jul. 1983. 29(4): p. 551-559.
Engin, A.E. and Chen, S.-M., "Statistical Data Base for the Biomechanical Properties of the Human Shoulder Complex—II: Passive Resistive Properties Beyond the Shoulder Complex Sinus," J Biomech Eng, Aug. 1986. 108(3): p. 222-227.
Maurel, W., "3D Modeling of the Human Upper Limb Including the Biomechanics of Joints, Muscles and Soft Tissues," in Informatique, Jan. 1999, École Polytechnique Fédérale de Lausanne (EPFL): Lausanne, Suisse. p. 204.
Veeger, H.E.J. and Yu, B., "Orientation of axes in the elbow and forearm for biomechanical modeling," in Biomedical Engineering Conference, Mar. 1996, Proceedings of the 1996 Fifteenth Southern, Mar. 1996.
Wilhelms, J. and A. Van Gelder, Fast and easy reach-cone joint limits. J. Graph. Tools, 2002. 6(2): p. 27-41.
Doody, S.G., L. Freedman, and J.C. Waterland, Shoulder movements during abduction in the scapular plane. Arch Phys Med Rehabil, 1970. 51(10): p. 595-604.
Poppen, N.K. and P.S. Walker, Normal and abnormal motion of the shoulder. J Bone Joint Surg Am, 1976. 58(2): p. 195-201.
Bagg, S.D. and W.J. Forrest, *A biomechanical analysis of scapular rotation during arm abduction in the scapular plane.* Am J Phys Med Rehabil, 1988. 67(6): p. 238-45.
Johnson, G.R., P.R. Stuart, and S. Mitchell, *A method for the measurement of three-dimensional scapular movemen.* Clin Biomech (Bristol, Avon), 1993. 8(5): p. 269-73.
McQuade, K.J. and G.L. Smidt, *Dynamic scapulohumeral rhythm: the effects of external resistance during elevation of the arm in the scapular plane.* J Orthop Sports Phys Ther, 1998. 27(2): p. 125-33.

(56) References Cited

OTHER PUBLICATIONS van der Helm, F.C. and G.M. Pronk, *Three-dimensional recording and description of motions of the shoulder mechanism*. J Biomech Eng, 1995. 117(1): p. 27-40.

Ludewig, P.M., T.M. Cook, and D.A. Nawoczenski, *Three-dimensional scapular orientation and muscle activity at selected positions of humeral elevation*. J Orthop Sports Phys Ther, 1996. 24(2): p. 57-65.

Meskers, C.G.M., et al., *3D shoulder position measurements using a six-degree-of-freedom electromagnetic tracking device*. Clinical Biomechanics, 1998. 13(4-5): p. 280-292.

Notification of and Extended European Search Report issued in European Patent Application 16182472.7, "Method and System for Vision Measure for Digital Human Models," dated Jan. 9, 2017.

Zhou, et al., "Simulating Complex Automotive Assembly Tasks Using the HUMOSIM Framework," Jun. 9, 2009, 14 pages, ISSN 0148-7191, DOI 10.4271/2009-01-2279 Retrieved from the Internet: citeseerx.ist.psu.edu/viewdoc/download?do =10.1.1.458.5238 &rep=repl&type=pdf [retrieved on Jan. 9, 2017].

Masih-Tehrani, Behdad, and Farrokh Janabi-Sharifi, "Kinermatic Modeling and Analysis of the Human Workspace for Visual Perceptibility," International Journal of Industrial Ergonomics 38.1 (2008), pp. 73-89, available online Nov. 28, 2007.

Kim, K. Han, et al., "The Role of Visual and Manual Demand in Movement and Posture Organization," No. 2006-01-2331, SAE Technical Paper, Published Jul. 4, 2006, Abstract only.

Yang, Jingzhou, et al., "Validation of Predicted Posture for the Virtual Human Santos TM" First International Conference on Digital Human Modeling, Jul. 22-27, 2007, pp. 500-510.

Christensen, J.M., et al., "Man-Systems Integration Standards," (NASA-STD-3000), N.A.a.S. Administration, Editor. 1989, National Aeronautics and Space Administration: Houston, TX, USA vol. 2, 617 pages. Retrieved from the Internet URL: https://msis.jsc.nasa.gov/Volume1.htm.

Notification of and Extended European Search Report issued in European Patent Application 16203060.5, "Method and System of Constraint-Based Optimization of Digital Human Upper Limb Models," dated Apr. 28, 2017.

Charbonnier, et al., "A patient-specific measurement technique to model shoulder joint kinematics," Orthopaedics & Traumatology: Surgery & Research, vol. 100, No. 7, Nov. 1, 2014, pp. 715-719.

Wilhelms, et al., "Fast and Easy Reach-Cone Joint Limits," Aug. 2, 2001, 10 pages, XP055365812, Retrieved from the Internet: https://pdfs.semanticscholar.org/d535/e562effd08694821ea6a8a5769fe10ffb5b6.pdf [retrieved on Apr. 20, 2017].

Xiang, Y., et al., "Human lifting simulation using a mult-objective optimization approach", Multibody Syst Dyn (2010) 23:431-451.

Hue, V., et al., "On Realistic Human Motion Simulation for Virtual Manipulation Tasks", 10th Intl. Conf. on Control, Automation, Robotics and Vision, Hanoi, Vietnam, Dec. 17,20, 2008.

Yang et al. "Multi-objective optimization-based method for kinematic posture prediction: development and validation." Robotica 29.2 (2011): 245-253. (Year: 2011).

\* cited by examiner

METHOD AND SYSTEM OF CONSTRAINT-BASED OPTIMIZATION OF DIGITAL HUMAN UPPER LIMB MODELS

BACKGROUND

A virtual manikin is a computer-generated image of an entity (i.e., a person or thing) that can be manipulated to assume a position or pose an actual person or thing could naturally assume. For the embodiments described herein, the entity is a human body or a portion of a human body, although in general the describe concepts could be applied to other entities, for example real animals or imaginary creatures.

A virtual manikin may include a simplified upper limb kinematic chain that consists of four segments: a clavicle, a humerus, a forearm and a hand. This kinematic chain may include, for example, nine degrees of freedom (DOF), allowing the end-effector of the chain (i.e., the hand) to be moved to engage a specified target such as a handle, a drill or a screwdriver.

The kinematic chain may also include a range of motion (ROM) in terms of spatial bounds for each DOF of the kinematic chain. This way of simulating the human upper limb is similar to what is seen in robot manipulators, for which nothing more than constant lower and upper bounds on each DOF are necessary to limit the movements of a redundant kinematic chain.

Virtual manikins often use an inverse kinematic (IK) posturing engine to find the configuration of the manikin (i.e., the value of each DOF) that positions the end-effector on the specified target. Although the IK posturing engine is quite efficient in finding a solution, the predicted postures lack robustness. A "lack of robustness" refers to the fact that a slight displacement of the target may lead to abrupt jumps in the DOF angles, which may result in an unrealistic human posture.

This lack of robustness is due, at least in part, to the redundancy of the kinematic chain. Kinematic chain redundancy refers to the fact that the kinematic chain can accommodate multiple ways to accomplish the same end-effector position. The redundancy exists because of a high number of DOFs (in this example, nine DOFs from the clavicle to the hand), with respect to the number of end-effector constraints (between 3 and 6 for the hand, for this example).

It is known that physiological dependencies exist between various DOFs of the human upper limb. For example, when the humerus is elevated in different planes of elevation, the clavicle and scapula segments follow a repeatable, non-linear pattern of motion, known as the "shoulder rhythm." Further, a non-linear relationship exists between the orientation of the humerus in space, and the limit of internal/external humerus axial rotation.

Among others, these physiological dependencies represent the complex physiological nature of the human upper limb, which is far more sophisticated than a robot manipulator. A complete integration of all these physiological dependencies is lacking in conventional virtual manikins found in the art.

The upper limb of virtual manikins known in the art thus involves (1) a redundancy in the kinematic chain, (2) a simplified kinematic chain that does not take into account the dependencies between each DOF, and (3) a simplification and (sometimes) under/overestimation of ROM that come from outdated databases. The direct consequence is a solution space that is too large, which may lead to unwanted oscillation in the kinematic chain and poor robustness of the predicted posture.

From a user's perspective, posturing the virtual manikin with a conventional upper limb model can become a challenging and cumbersome task. The posturing task may require a substantial amount of time, reducing the time available for biomechanical analysis of the resulting posture. Moreover, with such model, the users have less confidence in the predicted postures, given that some postures may seem impossible to achieve in reality.

SUMMARY

The described embodiments provide several improvements to conventional techniques for simulating the upper limb portion of a virtual manikin. For example, the described embodiments use biomechanical information related to upper limb biomechanics gathered from multiple sources. Further, the described embodiments use specific information related to the kinematics and the ROM of each DOF of the upper limb.

The described embodiments propose an improved management of the upper limb kinematic chain redundancy by imposing:
1. A pre-computed physiological rhythm that drives the clavicle DOF, and
2. Conical reach cones that simulate physiological ROM of the clavicle, humerus and wrist joints.

The proposed humerus ROM of the described embodiments may cover three different percentiles (i.e., 5, 50 and 95th) of the estimated population. Meanwhile, the proposed wrist ROM of the described embodiments may cover four different types of hand openings using distinct reach cones (i.e., fully opened fist, holding a small cylinder (e.g., 25 mm diameter), holding a large cylinder (e.g., 50 mm diameter), and a fully closed fist).

Advantages of the smart upper limb model may include the absence of clavicle oscillation and an improved robustness. These improvements are expected to contribute in reducing the proportion of time dedicated in positioning the manikin, thus increasing the proportion of time dedicated to posture analysis.

When comparing the accuracy of the constrained smart upper limb model to a model with only lower/upper bounds constraints, no significant additional time was required by the IK posturing engine of the described embodiments in order to find a solution for the smart model. Due to its more constrained nature (i.e., reduced number of DOF and solution space), the model of the described embodiments outperforms the less constrained lower/upper bounds model.

In one aspect, the invention is an upper limb model of a virtual manikin, including a data conversion engine configured to produce converted data based on one or more data sets. Each data set may represent dependencies between elements of a kinematic chain. The upper limb model further includes a model of the kinematic chain configured to generate one or more constraints based on the converted data, and a posturing engine configured to determine, based on the one or more constraints, a trajectory from a first position to a second position.

In one embodiment, the kinematic model further includes a rendering engine configured to render a posture corresponding to the second posture. In another embodiment, the elements of the kinematic model include one or more of a clavicle, a scapula, a humerus, a forearm and a hand.

In one embodiment, the dependencies relate to one or more degrees of freedom associated with at least one of the elements of the kinematic model. In another embodiment, the one or more data sets include experimental data. In another embodiment, the kinematic model includes at least one of a clavicle-scapula-humerus (CSH) model and a clavicle-humerus (CH) model. The humerus joints of the CSH model may be connected to the humerus joints of the CH model, and the elbow joints of the CSH model may be connected to the elbow joints of the CH model. The converted data may be provided to the CSH model as input for characterizing behavior of the CH model.

In one embodiment the one or more constraints includes at least one of (i) clavicle rhythm coefficients and (ii) a reach cone associated with a kinematic model element.

In another embodiment, the posturing engine includes a non-linear solver that is configured to perform one or more of (i) verify that each constraint is enforced, and (ii) determine constraint gradients indicative of search direction in a solution space.

In another aspect, the invention is a method of determining an end effector trajectory of a virtual manikin upper limb, including producing, with a data conversion engine, converted data based on one or more data sets. Each data set may represent dependencies between elements of a kinematic chain. The method further includes generating, with a model of a kinematic chain, one or more constraints based on the converted data. The method also includes determining, with a posturing engine, the end effector trajectory from a first position to a second position. The end effector trajectory may be determined based on the one or more constraints.

One embodiment further includes rendering, using a rendering engine, a posture corresponding to the second posture. Another embodiment further includes acquiring the data sets from experimental data.

In one embodiment, the generating further includes executing at least one of a clavicle-scapula-humerus (CSH) model and a clavicle-humerus (CH) model. The method may further include connecting the humerus joints of the CSH to the humerus joints of the CH model, and connecting the elbow joints of the CSH model to the elbow joints of the CH model. The method may further include providing the converted data to the CSH model as input for characterizing behavior of the CH model. In another embodiment, the one or more constraints includes at least one of (i) clavicle rhythm coefficients and (ii) a reach cone associated with a kinematic model element.

One embodiment further includes performing, with a non-linear solver, one or more of (i) verification that each constraint is enforced, and (ii) determination of constraint gradients indicative of a search direction in a solution space.

In yet another aspect, the invention is a non-transitory computer-readable medium configured to store instructions for determining an end effector trajectory of a virtual manikin upper limb. The instructions, when loaded and executed by a processor, cause the processor to produce, with a data conversion engine, converted data based on one or more data sets. Each data set may represent dependencies between elements of a kinematic chain. The instructions further cause the processor to generate, through the use of a model of a kinematic chain, one or more constraints based on the converted data. The instructions further cause the processor to determine, through the use of a posturing engine, the end effector trajectory from a first position to a second position. The end effector trajectory may be determined based on the one or more constraints.

In one embodiment, the instructions further cause the processor to render, using a rendering engine, a posture corresponding to the second posture.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale; emphasis instead being placed upon illustrating embodiments of the present invention.

DETAILED DESCRIPTION OF THE INVENTION

A description of example embodiments of the invention follows.

The teachings of all patents, published applications and references cited herein are incorporated by reference in their entirety.

The smart upper limb model applies physiological constraints on the kinematic chain of the upper limb, in order to reduce the number of possible solutions. To do so, the model needs information related to these physiological constraints, such as the clavicle rhythm and the segmental reach cones. These constraints are estimated during the "creation" step of the model. During the "application" step, these constraints are further applied to the upper limb portion of the virtual manikin, which is driven by an optimization-based inverse kinematic (IK) posturing engine.

Figure 1A:
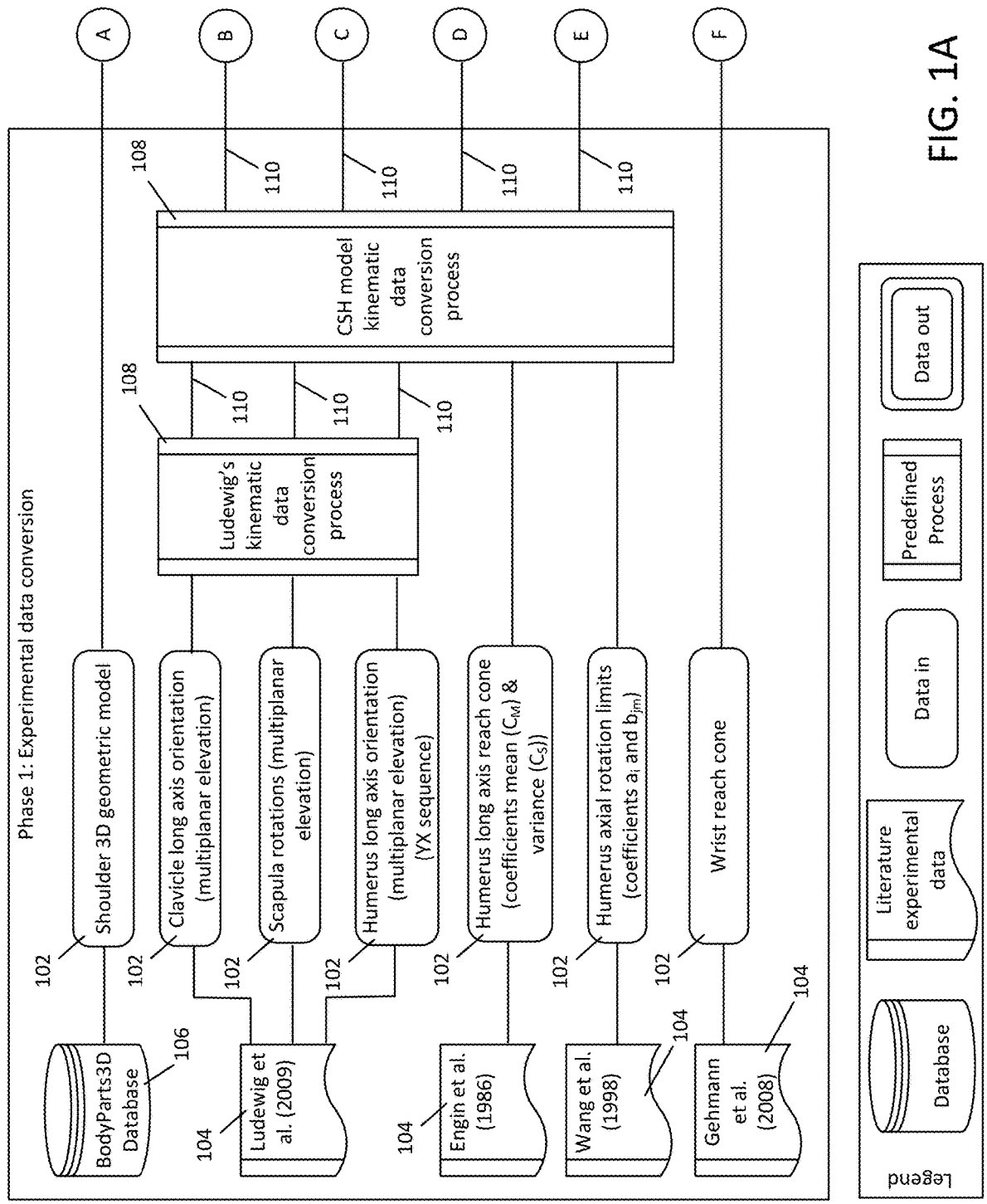
FIG. 1A illustrates the first phase of the creation step according to one or more described embodiments of the invention.
Figure 1B:
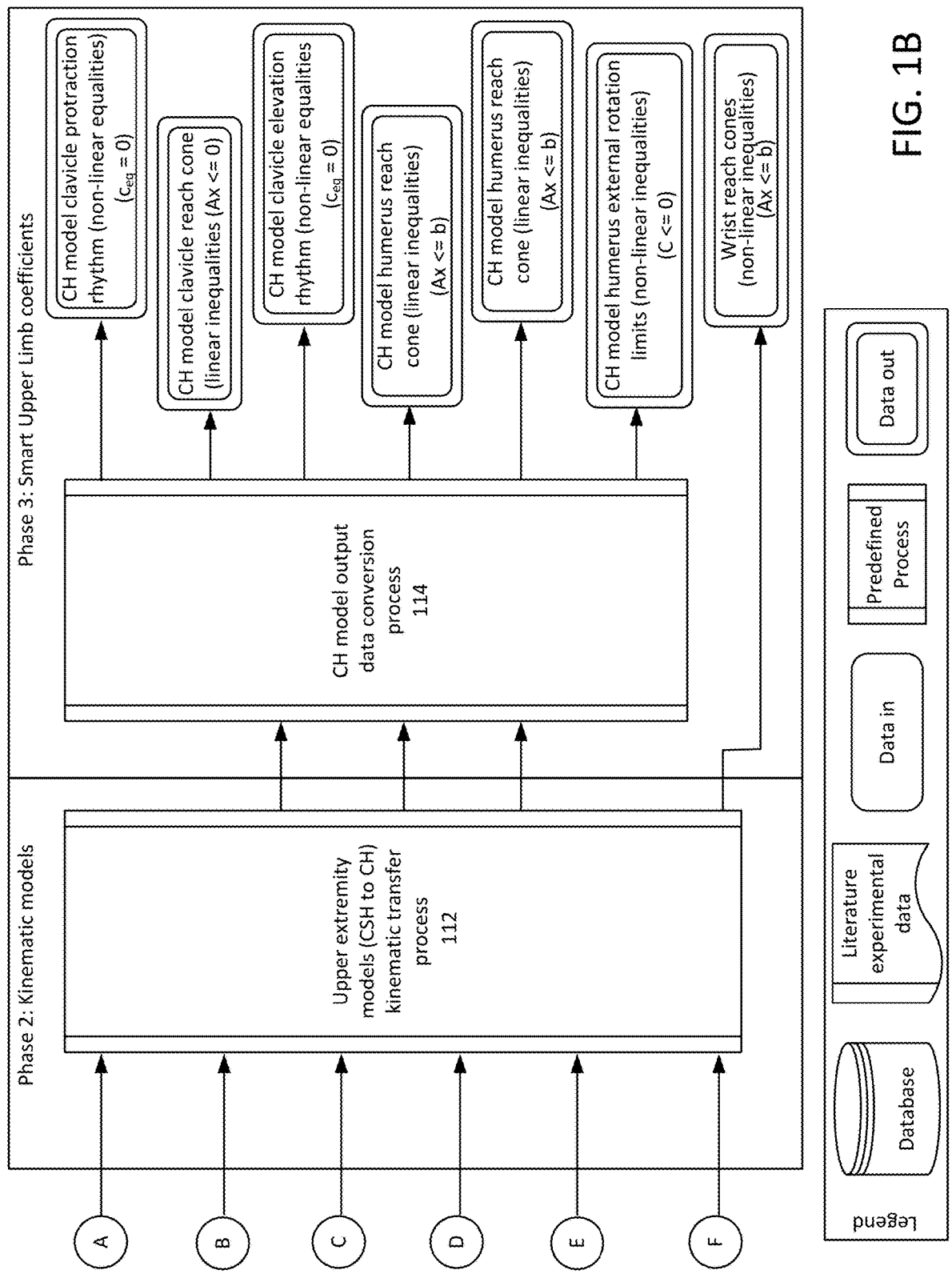
FIG. 1B illustrates the second and third phase of the creation step according to the invention.

The creation step is further divided into 3 phases, illustrated in FIGS. 1A and 1B. During phase 1, shown in FIG.

1A, experimental data 102 is gathered from various literature studies 104, or taken from a database 106. Some of this data is then converted by one or more conversion processes 108 into a convenient form 110, in order to be used by two upper limb models 112 in phases 2 (shown in FIG. 1B). The example embodiment of FIGS. 1A through 1F may use experimental data from the references listed below, although other embodiments may use other references, instead of or with some or all of the following references:

de Groot, J. H. and R. Brand, "A three-dimensional regression model of the shoulder rhythm," Clin Biomech (Bristol, Avon), 2001. 16(9): p. 735-43.

Grewal, T.-J. and C. R. Dickerson, "A novel three-dimensional shoulder rhythm definition that includes overhead and axially rotated humeral postures," Journal of biomechanics, 2013. 46(3): p. 608-611.

Inman, V. T., J. B. Saunders, and L. C. Abbott, "Observations of the function of the shoulder joint," Clin Orthop Relat Res, 1944(330): p. 3-12.

Ludewig, P. M., et al., "Motion of the shoulder complex during multiplanar humeral elevation." J Bone Joint Surg Am, 2009. 91(2): p. 378-89.

McClure, P. W., et al., "Direct 3-dimensional measurement of scapular kinematics during dynamic movements in vivo" J Shoulder Elbow Surg, 2001. 10(3): p. 269-77.

Wang, X., et al., "Three-dimensional modelling of the motion range of axial rotation of the upper arm," J Biomech, 1998. 31(10): p. 899-908.

Delfs, N., "Manikin in Time; Development of the Virtual Manikin with External Root and Improved Inverse Kinematics, in Mathematical Sciences," 2012, University of Gothenburg: Gothenburg. p. 40.

Christiensen, J. M. and J. W. McBarron, "Man-Systems Integration Standards," (NASA-STD-3000), N.A.a.S. Administration, Editor. 1989, National Aeronautics and Space Administration: Houston, Tex., USA.

Diffrient, N., A. Tilley, and D. Harman, "Humanscale 7/8/9," 1981, Massachusetts Institute of Technology: Cambridge, Mass. p. 52.

Engin, A. E. and S. M. Chen, "Statistical data base for the biomechanical properties of the human shoulder complex—I: Kinematics of the shoulder complex," J Biomech Eng, 1986. 108(3): p. 215-21.

Turner, S. T. and A. E. Engin, "Three-dimensional kinematic modelling of the human shoulder complex—Part II: Mathematical modelling and solution via optimization," J Biomech Eng, 1989. 111(2): p. 113-21.

Gehrmann, S. V., R. A. Kaufmann, and Z. M. Li, "Wrist circumduction reduced by finger constraints," J Hand Surg Am, 2008. 33(8): p. 1287-92.

Edelsbrunner, H., D. Kirkpatrick, and R. Seidel, "On the shape of a set of points in the plane," Information Theory, IEEE Transactions on, 1983. 29(4): p. 551-559.

Engin, A. E. and S. M. Chen, "Statistical data base for the biomechanical properties of the human shoulder complex—II: Passive resistive properties beyond the shoulder complex sinus," J Biomech Eng, 1986. 108(3): p. 222-7.

Maurel, W., "3d modeling of the human upper limb including the biomechanics of joints, muscles and soft tissues, in Informatique," 1999, École Polytechnique Fédérale de Lausanne (EPFL): Lausanne, Suisse. p. 204.

Veeger, H. E. J. and B. Yu., "Orientation of axes in the elbow and forearm for biomechanical modelling," in Biomedical Engineering Conference, 1996., Proceedings of the 1996 Fifteenth Southern. 1996.

Wilhelms, J. and A. Van Gelder, "Fast and easy reach-cone joint limits," J. Graph. Tools, 2002. 6(2): p. 27-41.

Doody, S. G., L. Freedman, and J. C. Waterland, "Shoulder movements during abduction in the scapular plane," Arch Phys Med Rehabil, 1970. 51(10): p. 595-604.

Poppen, N. K. and P. S. Walker, "Normal and abnormal motion of the shoulder," J Bone Joint Surg Am, 1976. 58(2): p. 195-201.

Bagg, S. D. and W. J. Forrest, "A biomechanical analysis of scapular rotation during arm abduction in the scapular plane," Am J Phys Med Rehabil, 1988. 67(6): p. 238-45.

Johnson, G. R., P. R. Stuart, and S. Mitchell, "A method for the measurement of three-dimensional scapular movement," Clin Biomech (Bristol, Avon), 1993. 8(5): p. 269-73.

McQuade, K. J. and G. L. Smidt, "Dynamic scapulohumeral rhythm: the effects of external resistance during elevation of the arm in the scapular plane," J Orthop Sports Phys Ther, 1998. 27(2): p. 125-33.

van der Helm, F. C. and G. M. Pronk, "Three-dimensional recording and description of motions of the shoulder mechanism," J Biomech Eng, 1995. 117(1): p. 27-40.

Ludewig, P. M., T. M. Cook, and D. A. Nawoczenski, "Three-dimensional scapular orientation and muscle activity at selected positions of humeral elevation," J Orthop Sports Phys Ther, 1996. 24(2): p. 57-65.

Meskers, C. G. M., et al., "3D shoulder position measurements using a six-degree-of-freedom electromagnetic tracking device. Clinical Biomechanics, 1998," 13(4-5): p. 280-292.

Wu, G., van der Helm, F. C. T., Veeger, H. E. J., Makhsous, M., Van Roy, P., Anglin, C., . . . Buchholz, B., "ISB recommendation on definitions of joint coordinate systems of various joints for the reporting of human joint motion—Part II: shoulder, elbow, wrist and hand. Journal of Biomechanics," 38(5), 981-992, 2005 (doi:http://dx-.doi.org/10.1016/j.jbiomech.2004.05.042).

Figure 1C:
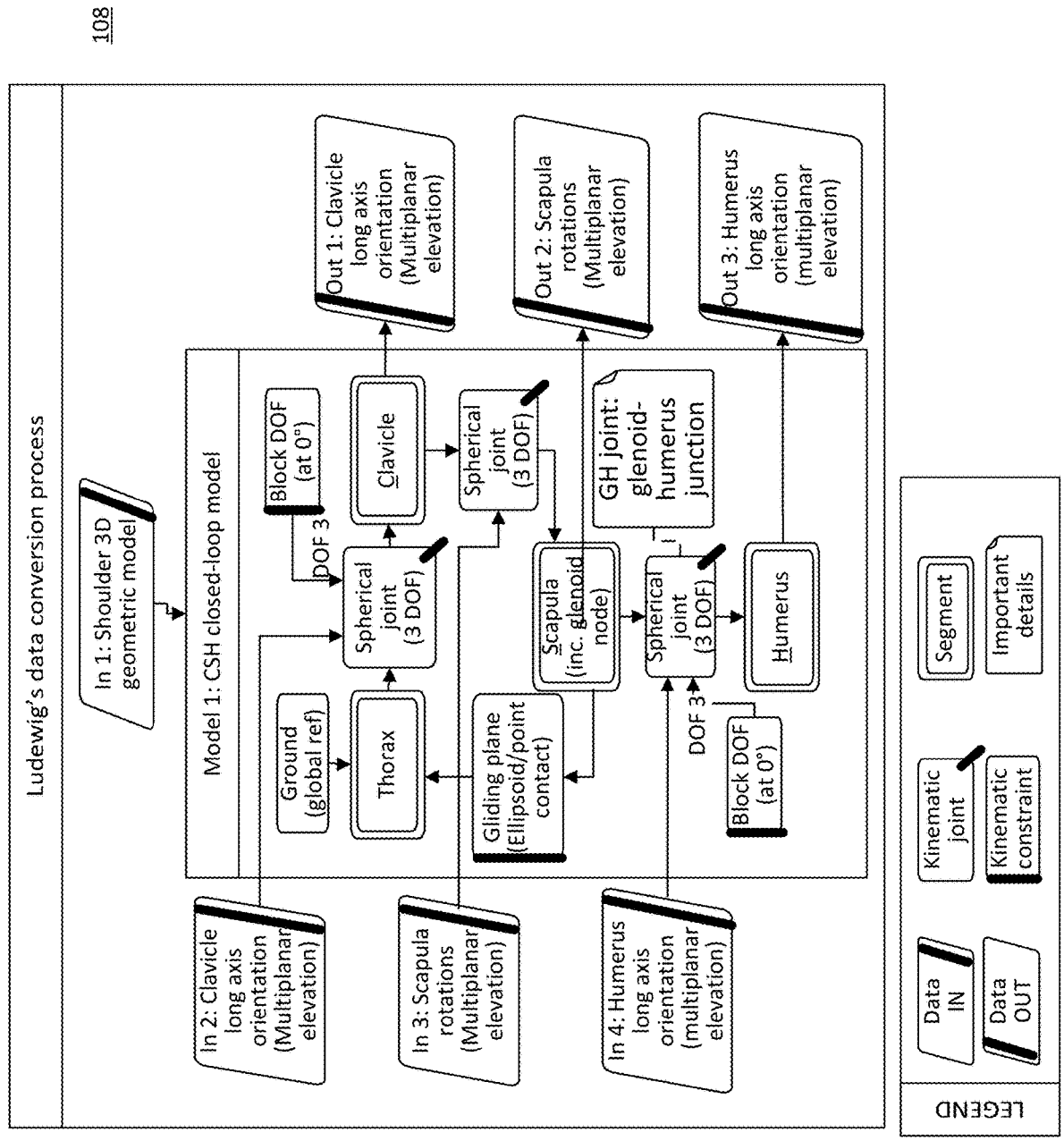
FIG. 1C illustrates a more detailed description of an example data conversion process according to the invention.
Figure 1D:
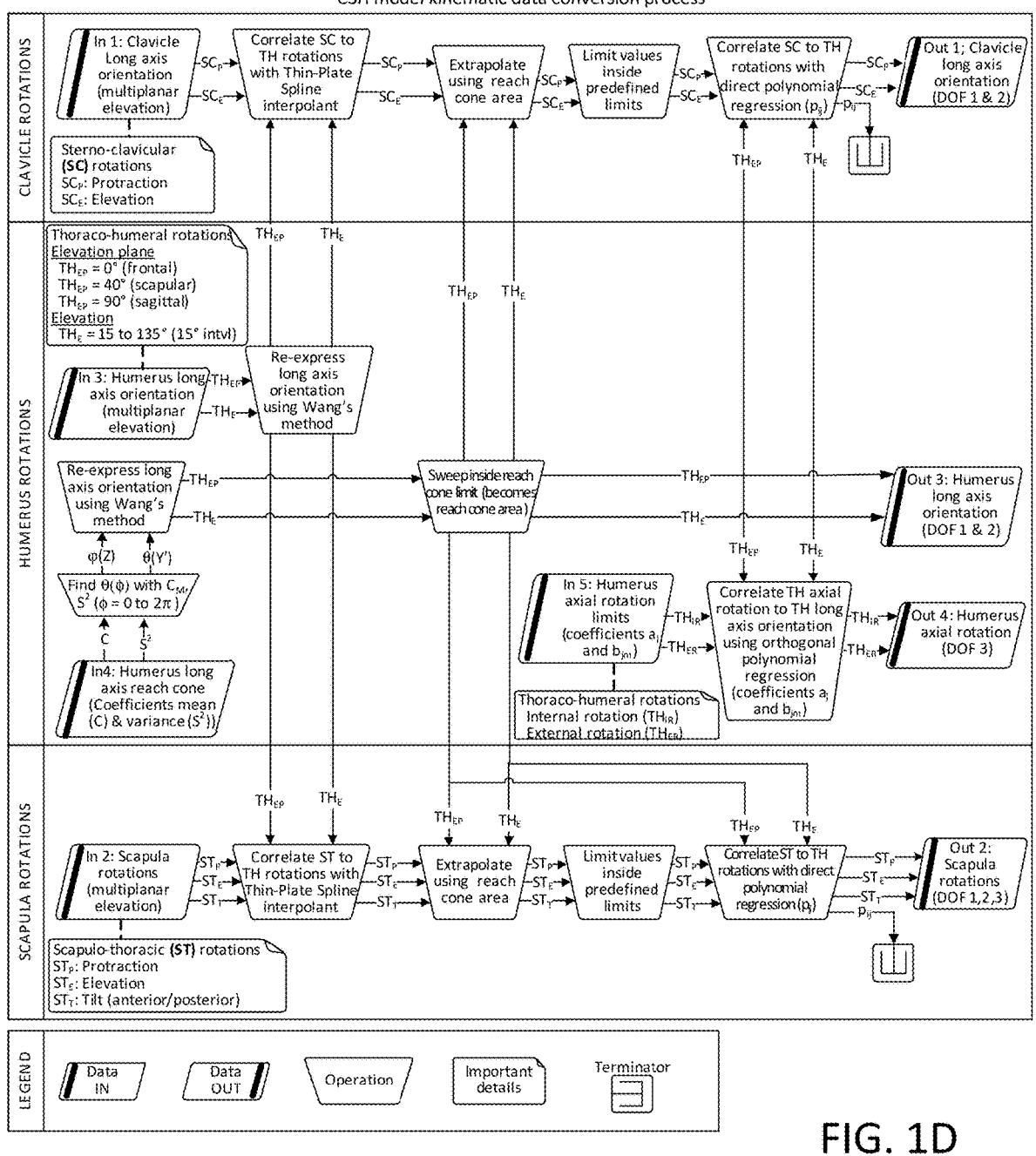
FIG. 1D illustrates a more detailed description of an example CSH model kinematic data conversion process according to the invention.

FIG. 1C provides a more detailed description of an example data conversion process 108, Ludewig's kinematic data conversion process, according to an embodiment of the invention. FIG. 1D provides a more detailed description of another example data conversion process 108, a CSH model kinematic data conversion process, according to an embodiment of the invention. The Ludewig's conversion process of FIG. 1C allows driving the CSH model with the experimental data of Ludewig et al. 2009. This data represents multiplanar elevation (frontal, scapular, and sagittal plane) from 15 to 135 degrees of elevation.

The CSH model is a closed-loop model consisting of 3 spherical joints, with 9 true degrees of freedom (DOF) and a gliding plane constraint between scapula and thorax. The local coordinate systems and DOFs respect the convention of Wu et al. (2005). While the long axis of the clavicle and humerus is free to move (represented by two DOF), the axial rotation (i.e., third DOF) was blocked at zero degrees with a kinematic constraint, since it was not useful in the process. The outputs of this process were the angle values of each DOF of the CSH model for the three distinct planes of elevation of Ludewig et al., 2009.

At the end of the process, these values are slightly different from Ludewig's data due to the application of the scapula-thorax gliding plane kinematic constraint. For that constraint, the proper portion of the thorax is simulated by an ellipsoid, while the proper portion of the scapula is simulated with contact nodes at relevant locations on its surface.

The CSH model kinematic data conversion process of FIG. 1D allows using the output data from the conversion process shown in FIG. 1C, along with two other experimental datasets (i.e. humerus long axis reach cone (Engin et al. 1986) and axial rotation limits (Wang et al. 1998). Various non-linear regressions between independent and dependent variables are computed. The two independent variables are the thoracohumeral (TH) elevation plane and elevation of the humerus, while the dependent variables were the DOF of the clavicle, scapula and the lower and upper limits of the third DOF of the humerus (i.e., axial rotation). First, a thin-plate spline interpolation between the various elevation planes of Ludewig's experimental data is performed. Thereafter, an extrapolation between the corresponding data and the humerus long axis external reach cone of Engin et al. 1986 experimental data was performed. Thereafter, the angle values that went beyond certain predefined limits were clamped to those limits. These limits were obtained from a previous careful review of various experimental studies of ROM estimation for each of the clavicle and scapula DOF. Finally, the regression coefficients were obtained between the independent and dependent variables, using a direct polynomial regression of third order. This process allowed sweeping the whole range of motion (ROM) of the shoulder while ensuring physiological movements of each segments of the CSH model. The outputs of this process were the angles of each DOF of the CSH model for each discrete point of the sweeping process.

Figure 1E:
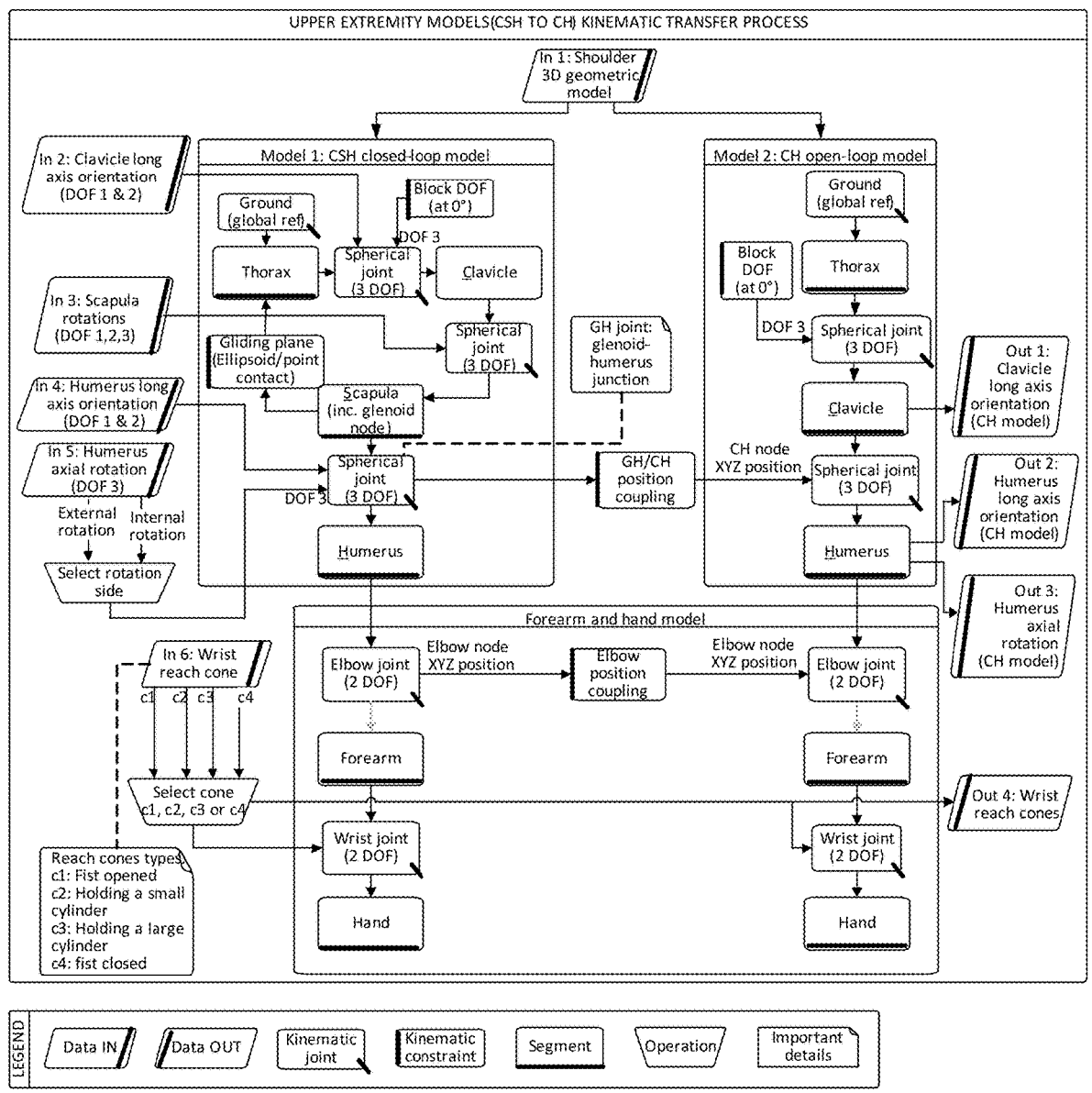
FIG. 1E illustrates a detailed description of example upper extremity models (CSH to CH) kinematic transfer process according to the invention.

The first model is a "clavicle-scapula-humerus" (CSH) closed-loop kinematic model, and is directly driven with the converted experimental data from phase 1. The second model is a "clavicle-humerus" (CH) opened-loop model, and is indirectly driven by the CSH model by connecting their respective humerus and elbow joints. This conversion between the CSH and CH models allows the described embodiments to obtain data that can be applied on the upper limb of a virtual manikin, which is usually simplified as a four-segment model without scapula. A detailed description of example upper extremity models upper extremity models (CSH to CH) kinematic transfer process 112 is shown in FIG. 1E. This process allows performing a coupling (i.e., kinematic transfer) between the CSH model and the simplified CH model, in order to transfer the ROM sweeping motion from the CSH model to the CH model. Both models had different kinematic configurations. The configurations of both models are shown in the block. As with the CSH model, the axial rotation (i.e., third DOF) of the clavicle of the CH model is blocked at zero degrees with a kinematic constraint, since it was not useful in the process. The CH model was coupled to the CSH model at two of their common joints (i.e., glenohumeral and elbow). The coupling had the form of a direct correspondence between the XYZ positions of these joints. The three first outputs of this process were the angles values of all the DOF of the CH model (i.e., clavicle and humerus) for each discrete point of the sweeping process. Moreover, four different versions of wrist reach cones were extracted from the study of Gehrmann et al., 2008. These different cones correspond to four different hand openings (fist closed, holding a 25 and 50 cm cylinder and fully opened hand). These cones did not interfere with the shoulder portion of the CSH and CH model. However, they are shown here along with the forearm and hand model kinematic configuration. This allows understanding the kinematic configuration of the forearm and hand for the whole upper limb of the virtual manikin and where the wrist cones were connected.

Figure 1F:
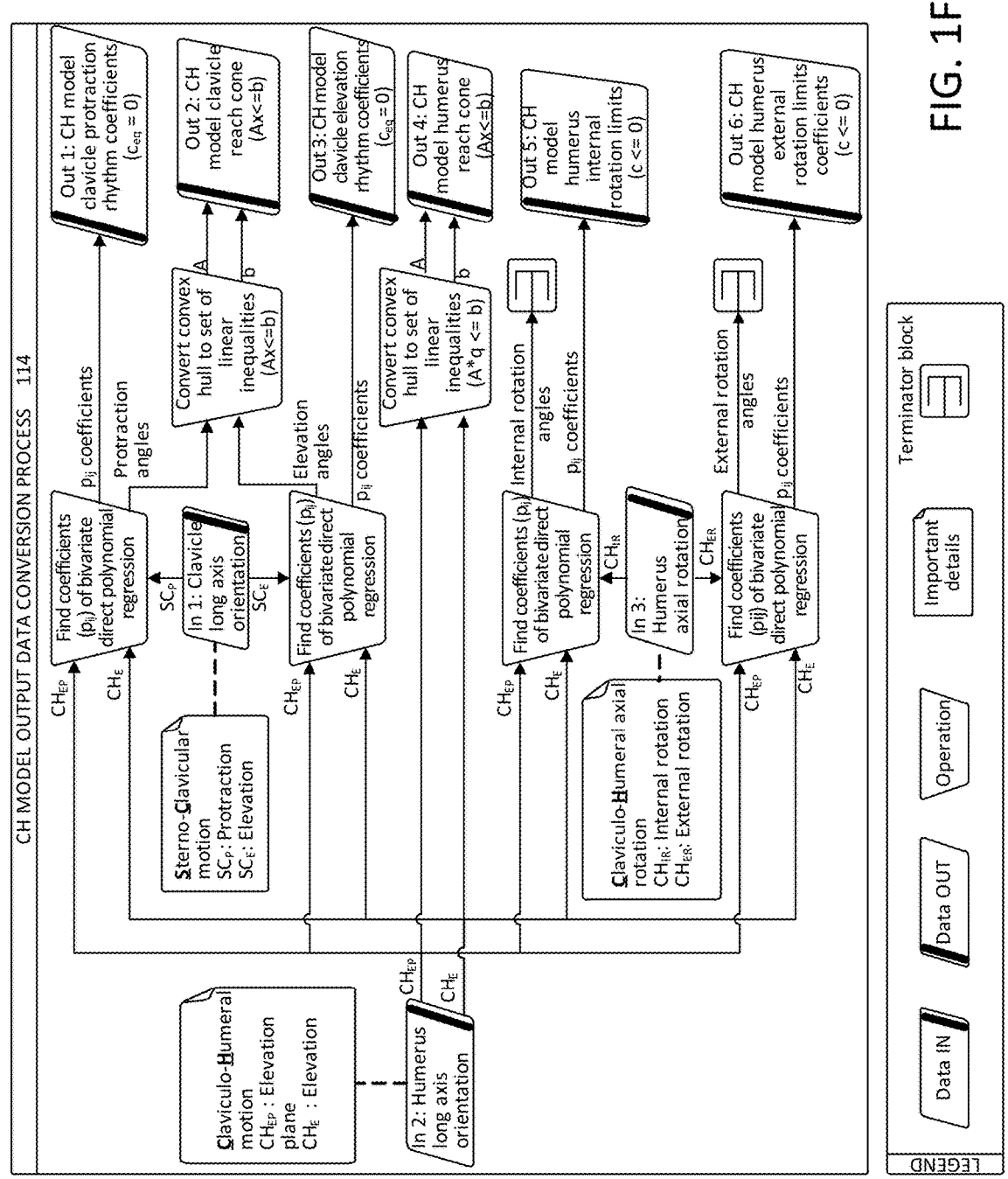
FIG. 1F illustrates a detailed description of an example CH model output data conversion process according to the invention.

In phase 3, once the kinematic of the CH model is obtained, the clavicle rhythm coefficients and the reach cones of the clavicle, humerus and wrist are estimated with a CH model output data conversion process 114. This information is further expressed as constraints in terms of one or more of (i) linear equalities, (ii) linear inequalities, (iii) non-linear equalities and (iv) non-linear inequalities, in order to feed the optimization-based IK engine. FIG. 1F provides a more detailed description of an example CH model output data conversion process 114, according to an embodiment of the invention. This process allows converting the CH model output data from the upper limb models 112 shown in FIG. 1E into convenient constraint coefficients, in order to constrain the non-linear optimization solver in a physiological manner. Various non-linear regressions between independent and dependent variables are computed. The two independent variables were the first two DOF of the glenohumeral (GH) joint (i.e., elevation plane and elevation), while the dependent variables are the two DOF of the clavicle and each of the lower and upper limits of the third DOF of the humerus (i.e., axial rotation).

Two types of constraints are derived: 1) clavicle rhythms and, 2) reach cones for the clavicle and humerus. The clavicle rhythm coupled the movements of the two independent humerus variables to each of the two DOF of the clavicle. Meanwhile, the reach cones establish a conical limit of the longitudinal axis of each of the clavicle and humerus segments, while considering only the boundary of the ROM sweeping. Various outputs were generated to feed to optimization solver. First, constraint coefficients (pij) are retrieved from the clavicle rhythm regressions imposed on each of its two DOF (protraction and elevation), and are further expressed as non-linear equalities (ceq=0). Furthermore, each reach cone (i.e. clavicle, humerus and wrist) is converted into a set of linear inequalities (Ax<=b), which represents the interior region of the cone. Finally, the regression coefficients (pij) of the humerus third DOF limits (i.e., internal rotations) are retrieved and further represent non-linear inequalities (c=0) imposed on those limits.

The optimization-based IK engine includes the smart upper limb constraints on-demand. In case the hand's effector is activated to reach a target, the posture engine is then configured to include the smart upper limb constraints in the problem to solve. These constraints (see "Data out" boxes in FIG. 1B) reduce the solution space by discarding any non-physiological postures of the upper-limb.

Internally, the non-linear solver used by the posture engine includes the constraints at two different levels. First, it verifies that each constraint is honored and held. Thereafter, associated constraints gradient (partial derivatives of the constraints regarding enabled manikin joint DOFs) are used to determine the search direction in the solution space. Eventually, when an optimal solution is found, the posture engine assigns it to the DOF of the manikin. The final posture is then displayed to the user.

A unique aspect of the described embodiments is the coupling together two upper limb models with different configurations (i.e., CSH and CH). This coupling allows the described embodiments to convert reach cones and rhythms experimentally measured on real shoulders configurations (i.e., CSH) into reach cones and rhythms dedicated to a simplified CH configuration. The described embodiments thus apply realistic physiological constraints to the CH model that are still used by many virtual manikins of the literature.

The upper limb model of the described embodiments exhibits an increased robustness with respect to an upper limb model with only lower/upper constant DOF bounds. This robustness is closely related to the behavior of the kinematic chain.

In some embodiments, and referring again to FIGS. 1A and 1B, the data conversion to produce converted data 110 is performed once, such that the resulting converted data may then be repeatedly used by the upper limb models 112. In other embodiments, the data conversion is performed for one or more executions of the upper limb models 112.

Figures 2A, 2B:
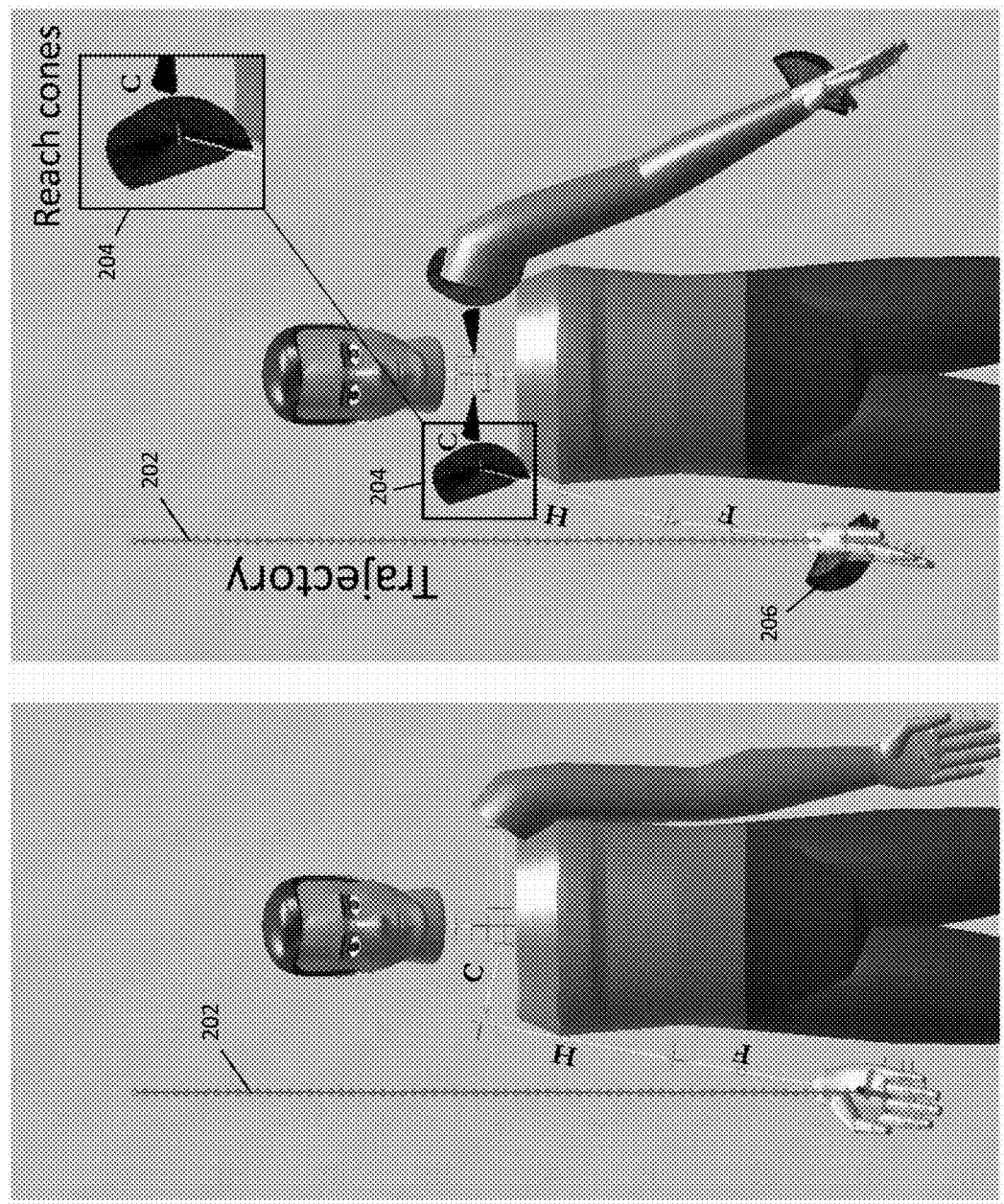
FIG. 2A illustrates a manikin with an example trajectory path according to a prior art upper limb model.
FIG. 2B illustrates a manikin with an example trajectory path according to one or more described embodiments of the invention.

In the example depicted in FIGS. 2A and 2B, a vertical trajectory 202 is located slightly in front and to the right of the manikin, from below the pelvis to above the head. FIG. 2A shows the imposed trajectory for a conventional upper limb model, and FIG. 2B shows the imposed trajectory for an upper limb model according to the described embodiments. In each of the FIGS. 2A and 2B, the forearm is identified by the letter "F," the humerus is identified by the letter "H," and the clavicle is identified by the letter "C." For FIG. 2B, the clavicle and humerus reach cones 204 and wrist reach cones 206 are also shown.

The robustness of the kinematic chain can be quantified by monitoring the various DOF of the clavicle, humerus and forearm during the vertical trajectory task. For this example, the task begins and ends at the bottom of the trajectory 202. A perfect robustness would be characterized by a smooth DOF curve with no abrupt changes, in which the ascending curve is identical as the descending curve.

Figure 3:
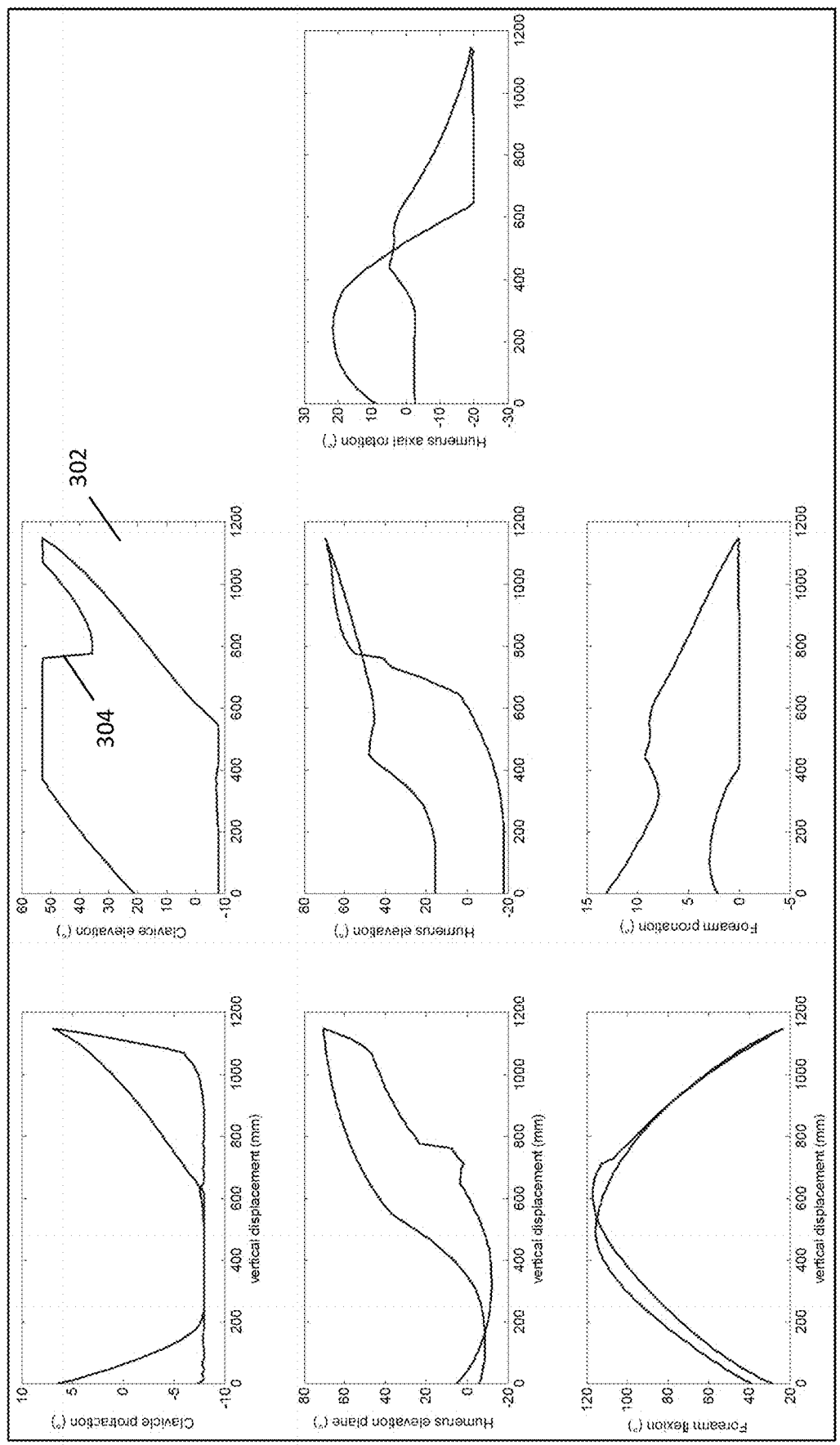
FIG. 3 illustrates various DOF angles, corresponding to the example of FIG. 2A.

The DOF angles for the upper limb model of FIG. 2A, with only lower/upper constant DOF bounds, are shown in FIG. 3. There are considerable differences in DOF angles between the ascending and descending portions of the task, especially for clavicle elevation as shown in graph 302. There are also abrupt changes in DOF angles, such as the change 304 exhibited for the clavicle elevation near 800 mm of vertical displacement. These results suggest that the conventional upper limb model suffers from a lack of robustness.

Figure 4:
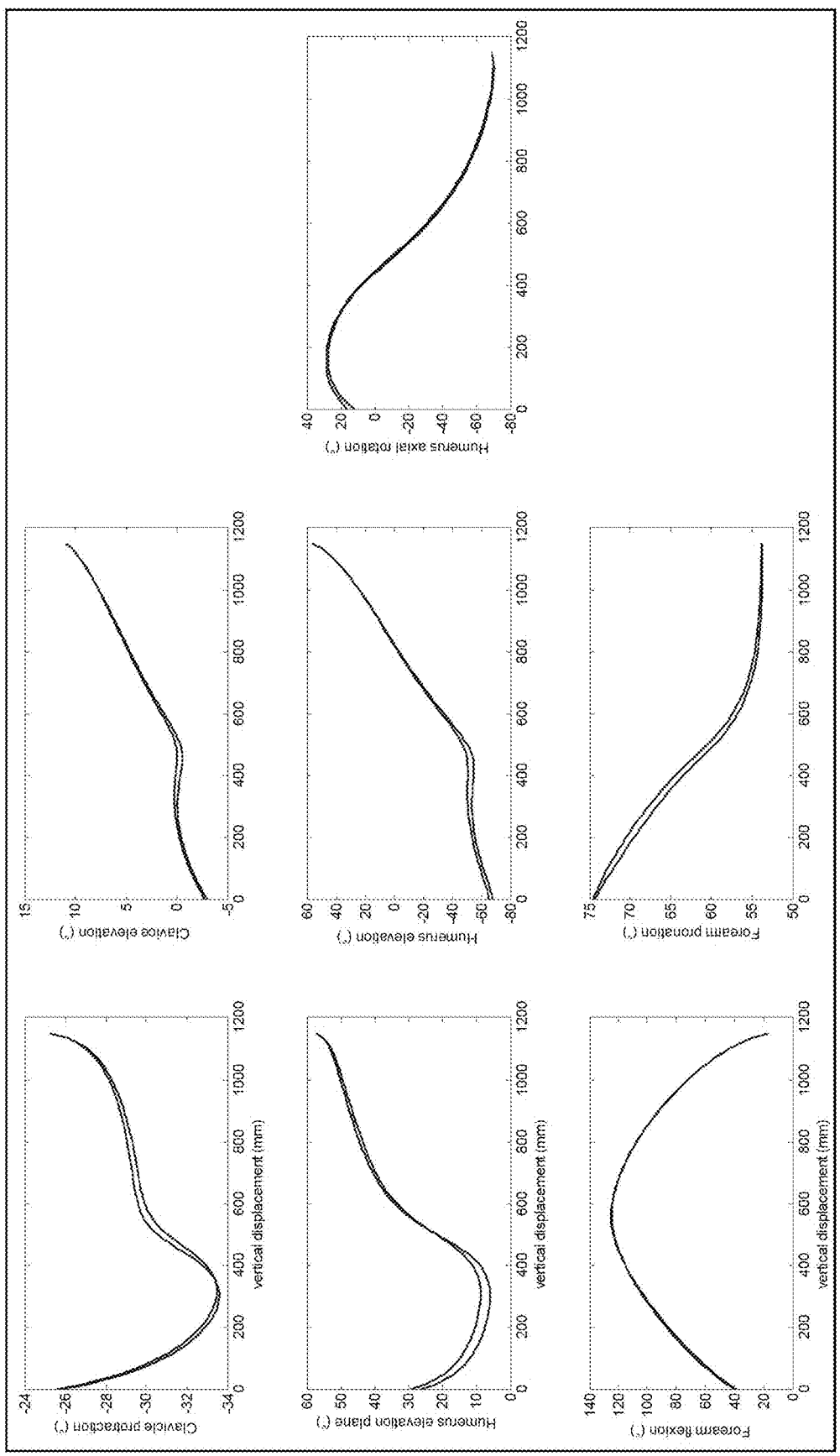
FIG. 4 illustrates various DOF angles, corresponding to the example of FIG. 2B.

The results for the smart upper limb model of the described embodiments are shown in FIG. 4. There are only slight differences between the DOF angles of the ascending and descending portions of the task, the two portions being nearly identical as shown in each graph. Moreover, the model according to the described embodiments depicted in FIG. 4 exhibits no abrupt changes of DOF angles such as change 304 in FIG. 3. These estimations are the direct result of applying a non-linear rhythm to the clavicle DOF, which forces its rotations to follow those of the humerus in a physiological manner. These results contribute to show that the robustness is considerably higher for the smart upper limb model of the described embodiments when compared to the model with only lower/upper constant DOF bounds.

Figure 5:
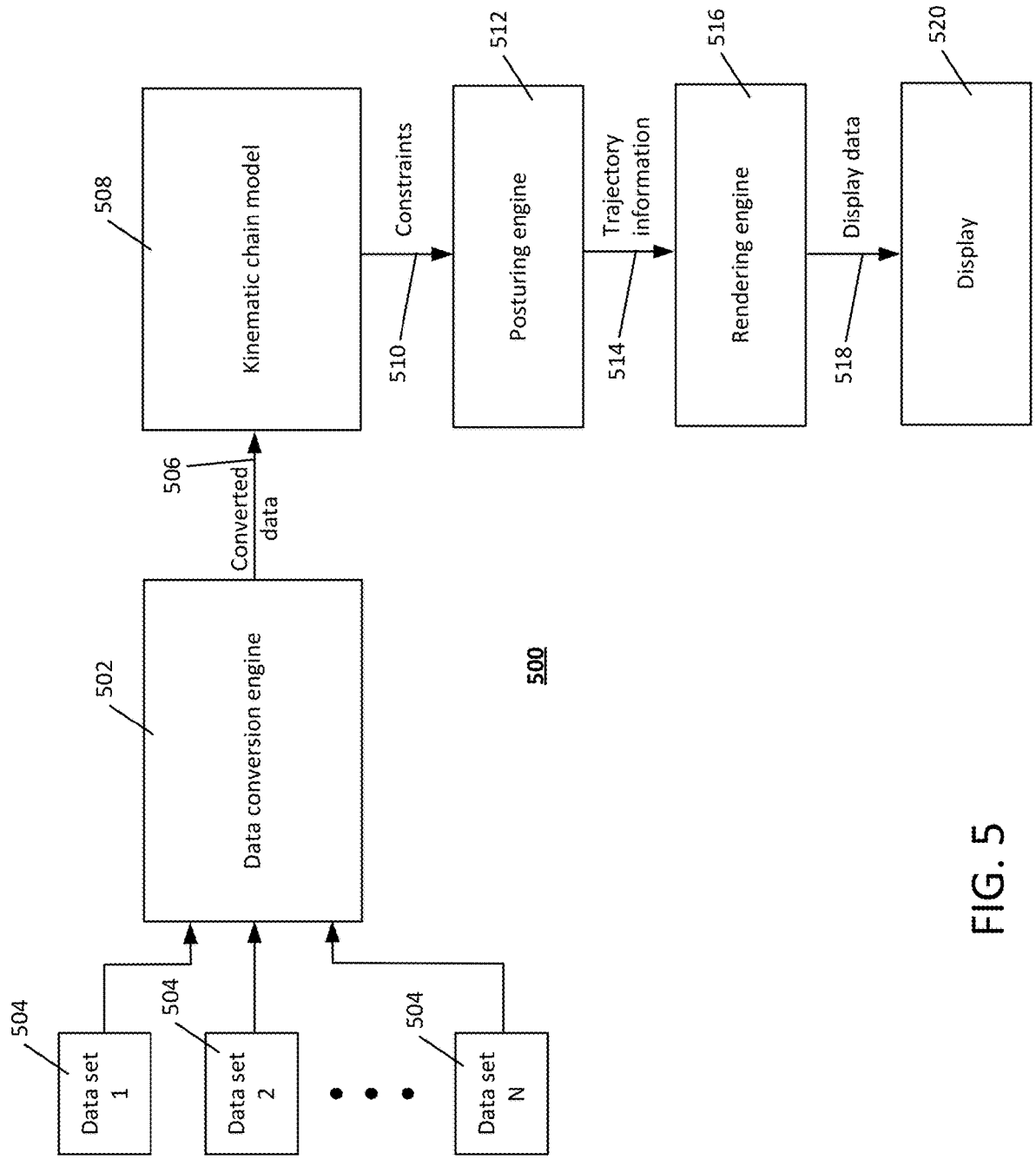
FIG. 5 illustrates an embodiment of a smart upper limb modeling system according to the invention.

FIG. 5 illustrates an embodiment of a smart upper limb modeling system 500 according to the invention. A data conversion engine 502 receives one or more data sets 504, each of which represents dependencies between elements of a kinematic chain, and produces one or more sets of converted data 506 using the process described above in FIGS. 1A-1F and/or the method 700 shown below in FIG. 7.

A kinematic chain model 508 generates one or more constraints 510 based on the converted data 506. A posturing engine 512 generates trajectory information 514 associated with the upper limb, based on the constraints 510.

In one embodiment, a rendering engine 516 generates display data 518, which is provided to a display component 520.

The data conversion engine 502, the kinematic chain model 508, the posturing engine 512 and the rendering engine 516 may be implemented by software or firmware code executed by a processor, by a hardware-based state machine or other hardware-based component such as an application specific integrated circuit (ASIC), or by a combination of a hardware implementation and software implementation.

Figure 6:
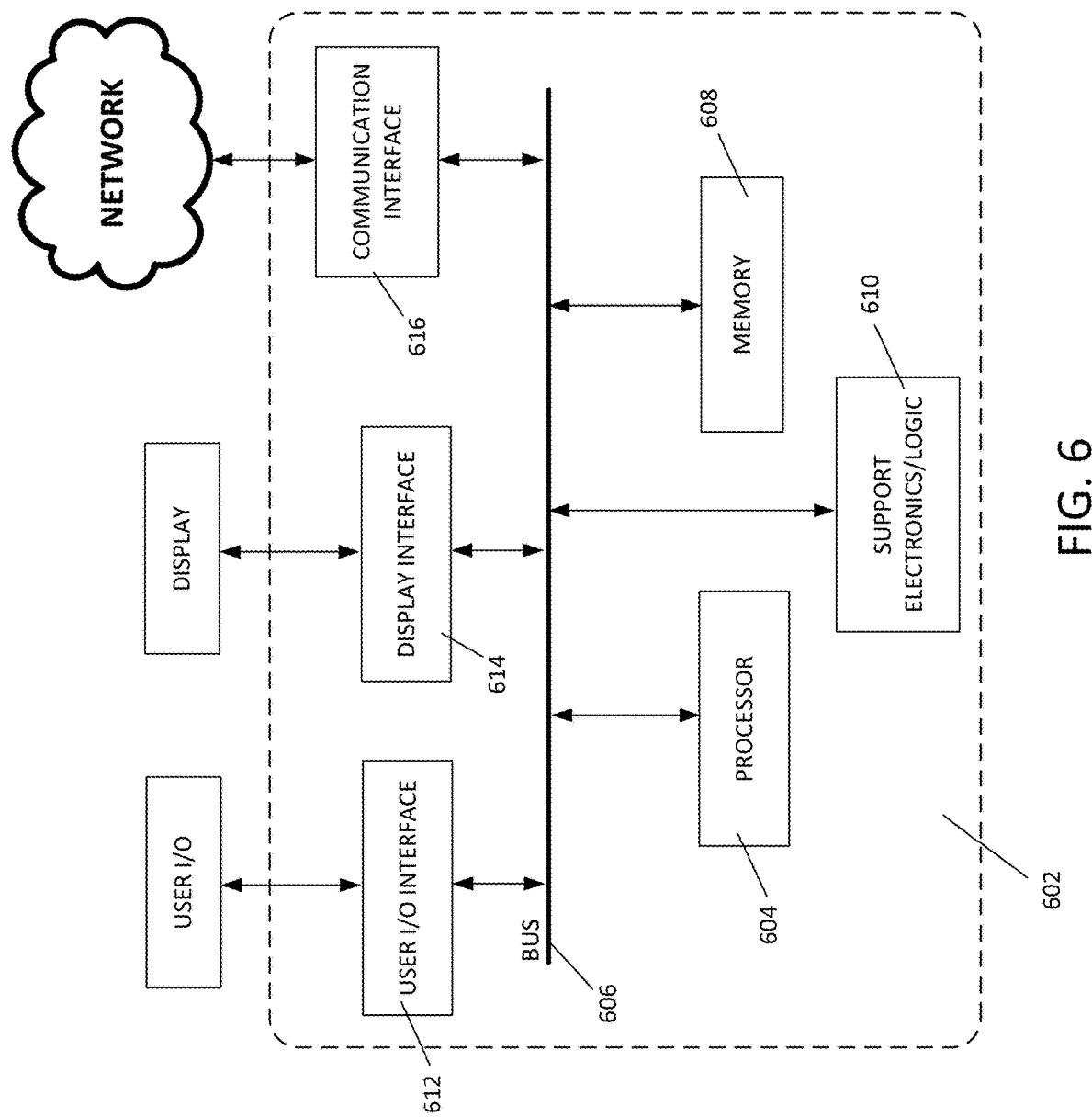
FIG. 6 illustrates one embodiment of a processor system that may be used to implement one or more of the component described and shown in FIG. 5.

FIG. 6 illustrates one embodiment of a processor system 602 that may be used to implement one or more of the component described and shown in FIG. 5. The processor system 602 includes a processor element 604 electrically coupled to a bus 606. The processor 604 accesses data and instruction code from a memory element 608 through the bus 606. The system 602 further includes various support electronics 610 connected to other elements of the processor system 602 through the bus 606 or directly through other communications paths. The system 602 also includes a user I/O interface 612 for communicating with various user I/O devices (e.g., keyboard, mouse, etc.), a display interface 614 for communicating with a display, and a communications interface 616 for communicating with external entities through a network (e.g., LAN, WAN or Internet). During operation, the processor system 602, via the processor element 604 and the data and instruction code stored in memory element 608, performs the steps the conversion process described above in FIGS. 1A-1F and/or the method shown below in FIG. 7.

Figure 7:
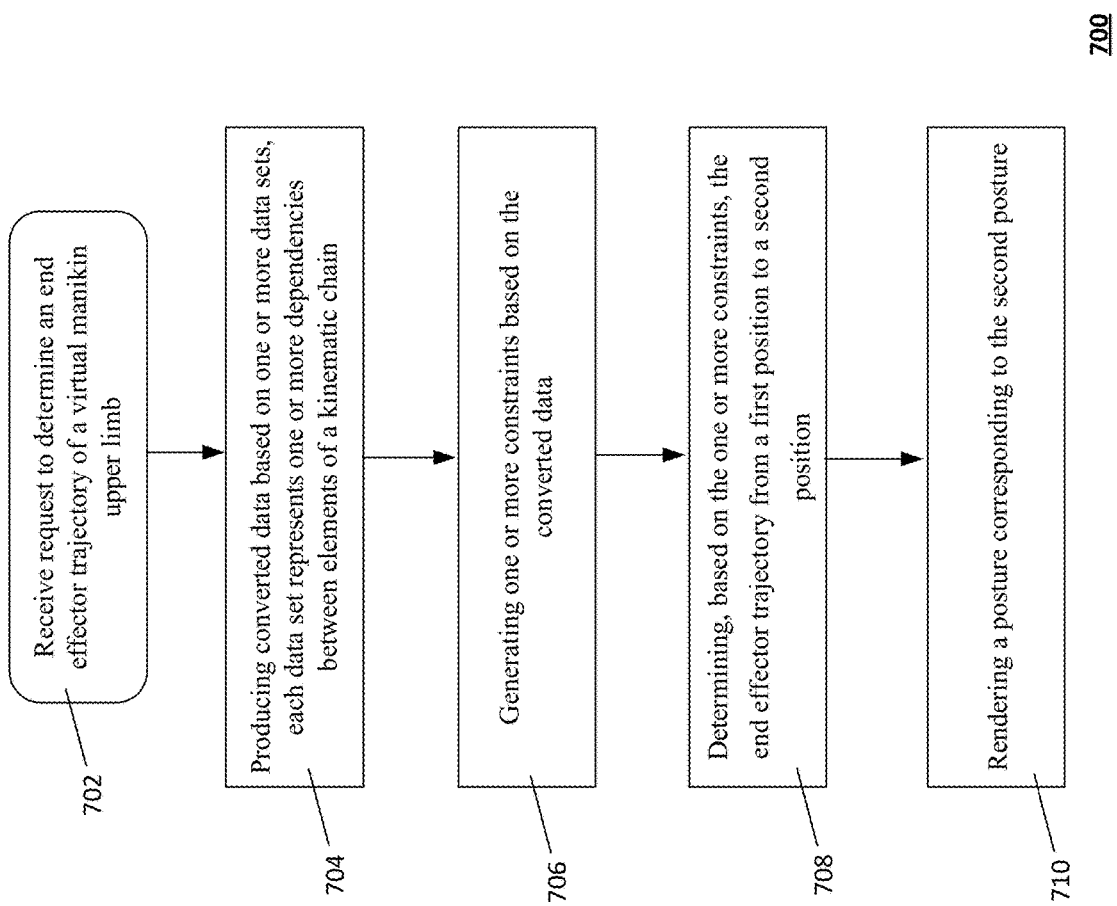
FIG. 7 illustrates one embodiment of a method of determining an end effector trajectory of a virtual manikin upper limb, according to the invention.

FIG. 7 illustrates one embodiment of a method 700 of determining an end effector trajectory of a virtual manikin upper limb, according to the invention. Upon receiving 702 a request to determine an end effector trajectory of a virtual manikin upper limb, the embodiment may include producing 704, with a data conversion engine, converted data based on one or more data sets. Each data set represents dependencies between elements of a kinematic chain. The embodiment may further include generating 706, with a model of a kinematic chain, one or more constraints based on the converted data. The embodiment may further include determining 708, with a posturing engine, the end effector trajectory from a first position to a second position. The end effector trajectory may be determined based on the one or more constraints. The embodiment may further include rendering 710, using a rendering engine, a posture corresponding to the second posture.

It will be apparent that one or more embodiments described herein may be implemented in many different forms of software and hardware. Software code and/or specialized hardware used to implement embodiments described herein is not limiting of the embodiments of the invention described herein. Thus, the operation and behavior of embodiments are described without reference to specific software code and/or specialized hardware—it being understood that one would be able to design software and/or hardware to implement the embodiments based on the description herein.

Further, certain embodiments of the example embodiments described herein may be implemented as logic that performs one or more functions. This logic may be hardware-based, software-based, or a combination of hardware-based and software-based. Some or all of the logic may be stored on one or more tangible, non-transitory, computer-readable storage media and may include computer-executable instructions that may be executed by a controller or processor. The computer-executable instructions may include instructions that implement one or more embodiments of the invention. The tangible, non-transitory, computer-readable storage media may be volatile or non-volatile and may include, for example, flash memories, dynamic memories, removable disks, and non-removable disks.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-implemented upper limb modeling system for modeling an upper limb of a virtual manikin, the system comprising:
   a processor; and
   a memory with computer code instructions stored thereon, the memory operatively coupled to the processor such that the computer code instructions cause the processor to implement:
   a data conversion engine configured to produce converted data based on one or more data sets, each data set representing dependencies between elements of a kinematic chain, the data conversion engine further configured to apply a scapula-thorax gliding plane kinematic constraint to the one or more data sets;
   a model of the kinematic chain configured to generate two or more constraints based on the converted data, the two or more constraints comprising both (i) clavicle rhythms and (ii) reach cones for a clavicle and a humerus;
   a posturing engine configured to determine, based on the two or more constraints, a trajectory of a hand-effector from a first position to a second position; and
   a rendering engine configured to render display data of a posture corresponding to the second position of the hand-effector, and to provide the display data to a display device.

2. The computer-implemented upper limb modeling system of claim 1, wherein the elements of the kinematic model include one or more of a clavicle, a scapula, a humerus, a forearm and a hand.

3. The computer-implemented upper limb modeling system of claim 1, wherein the dependencies relate to one or more degrees of freedom associated with at least one of the elements of the kinematic model.

4. The computer-implemented upper limb modeling system of claim 1, wherein the one or more data sets includes experimental data.

5. The computer-implemented upper limb modeling system of claim 1, wherein the kinematic model includes at least one of a clavicle-scapula-humerus (CSH) model and a clavicle-humerus (CH) model.

6. The computer-implemented upper limb modeling system of claim 5, wherein the humerus joints of the CSH model are connected to the humerus joints of the CH model, and the elbow joints of the CSH model are connected to the elbow joints of the CH model.

7. The computer-implemented upper limb modeling system of claim 6, wherein the converted data is provided to the CSH model as input for characterizing behavior of the CH model.

8. The computer-implemented upper limb modeling system of claim 1, wherein the posturing engine includes a non-linear solver that is configured to perform one or more of (i) verify that each constraint is enforced, and (ii) determine constraint gradients indicative of search direction in a solution space.

9. A method of determining an end effector trajectory of a virtual manikin upper limb, comprising:
   producing, with a data conversion engine, converted data based on one or more data sets, each data set representing dependencies between elements of a kinematic chain;
   applying, with the data conversion engine, a scapula-thorax gliding plane kinematic constraint to the one or more data sets;
   generating, with a model of a kinematic chain, two or more constraints based on the converted data, the two or more constraints comprising both (i) clavicle rhythms and (ii) reach cones for a clavicle and a humerus;
   determining, with a posturing engine, the end effector trajectory from a first position to a second position, the end effector trajectory determined based on the two or more constraints; and
   rendering, using a rendering engine, display data of a posture corresponding to the second position of the hand-effector, and providing the display data to a display device.

10. The method of claim 9, further including acquiring the data sets from experimental data.

11. The method of claim 9, wherein the generating further includes executing at least one of a clavicle-scapula-humerus (CSH) model and a clavicle-humerus (CH) model.

12. The method of claim 11, further including connecting the humerus joints of the CSH to the humerus joints of the CH model, and connecting the elbow joints of the CSH model to the elbow joints of the CH model.

13. The method of claim 11, further including providing the converted data to the CSH model as input for characterizing behavior of the CH model.

14. The method of claim 9, further including performing, with a non-linear solver, one or more of (i) verification that each constraint is enforced, and (ii) determination of constraint gradients indicative of a search direction in a solution space.

15. A non-transitory computer-readable medium configured to store instructions for determining an end effector trajectory of a virtual manikin upper limb, the instructions, when loaded and executed by a processor, cause the processor to:
   produce, with a data conversion engine, converted data based on one or more data sets, each data set representing dependencies between elements of a kinematic chain;
   apply, with the data conversion engine, scapula-thorax gliding plane kinematic constraint to the one or more data sets;
   generate, with a model of a kinematic chain, two or more constraints based on the converted data, the two or more constraints comprising both (i) clavicle rhythms and (ii) reach cones for a clavicle and a humerus; and
   determine, with a posturing engine, the end effector trajectory from a first position to a second position, the end effector trajectory determined based on the two or more constraints; and
   render display data of a posture corresponding to the second position of the hand-effector, and provide the display data to a display device.

16. The non-transitory computer-readable medium of claim 15, wherein the instructions further cause the processor to render, using a rendering engine, a posture corresponding to the second posture.

* * * * *